United States Patent
Lemm et al.

(10) Patent No.: US 8,415,374 B2
(45) Date of Patent: Apr. 9, 2013

(54) COMBINATIONS OF HEPATITIS C VIRUS INHIBITORS

(75) Inventors: Julie A. Lemm, Durham, CT (US); Stacey A. Voss, Wallingford, CT (US); Min Gao, Madison, CT (US); Susan E. Chaniewski, South Glastonbury, CT (US); Amy K. Sheaffer, Meriden, CT (US); Fiona McPhee, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 126 days.

(21) Appl. No.: 12/899,840

(22) Filed: Oct. 7, 2010

(65) Prior Publication Data

US 2011/0250176 A1    Oct. 13, 2011

Related U.S. Application Data

(60) Provisional application No. 61/250,648, filed on Oct. 12, 2009.

(51) Int. Cl.
*A61K 31/47* (2006.01)
*A61K 31/445* (2006.01)

(52) U.S. Cl.
USPC ............ 514/312; 514/313; 514/314; 514/315

(58) Field of Classification Search ............... 514/312, 514/313, 314, 315
See application file for complete search history.

(56) References Cited

U.S. PATENT DOCUMENTS

| | | | |
|---|---|---|---|
| 6,995,174 B2 * | 2/2006 | Wang et al. | 514/312 |
| 7,449,479 B2 | 11/2008 | Wang et al. | |
| 7,915,291 B2 * | 3/2011 | Wang et al. | 514/312 |
| 2006/0199773 A1 | 9/2006 | Sausker et al. | |
| 2010/0158862 A1 | 6/2010 | Kim et al. | |

FOREIGN PATENT DOCUMENTS

| | | |
|---|---|---|
| WO | WO 03/099274 | 12/2003 |
| WO | WO 2008/021927 | 2/2008 |
| WO | WO 2009/020825 | 2/2009 |
| WO | WO 2009/020828 | 2/2009 |
| WO | WO 2009/085659 | 7/2009 |
| WO | WO 2009/102325 | 8/2009 |

OTHER PUBLICATIONS

Lok, A.S. et al., "Combination Therapy with BMS-790052 and BMS-650032 Alone or with PegIFN/RBV Results in Undetectable HCV RNA Through 12 Weeks of Therapy in HCV Genotype 1 Null Responders", American Association for the Study of Liver Diseases (AASLD), Poster (Oct. 29, 2010).

Lok, A.S. et al., "Combination Therapy with BMS-790052 and BMS-650032 Alone or with PegIFN/RBV Results in Undetectable HCV RNA Through 12 Weeks of Therapy in HCV Genotype 1 Null Responders," Hepatology, vol. 52, No. 4 (Suppl.), No. LB-8, p. 877A (2010).

Lok, A.S. et al., "Quadruple Therapy with BMS-790052, BMS-650032 and PEG-IFN/RBV for 24 Weeks Results in 100% SVR12 in HCV Genotype 1 Null Responders", 46th Annual Meeting of the European Association for the Study of the Liver, Oral Presentation (Apr. 2, 2011).

* cited by examiner

*Primary Examiner* — Kevin E Weddington
(74) *Attorney, Agent, or Firm* — Pamela A. Mingo

(57) ABSTRACT

The present disclosure is generally directed to antiviral compounds, and more specifically directed to combinations of compounds which can inhibit Hepatitis C virus (HCV), compositions comprising such compounds, and methods for treating Hepatitis C using such combinations.

5 Claims, No Drawings

COMBINATIONS OF HEPATITIS C VIRUS INHIBITORS

CROSS-REFERENCE TO RELATED APPLICATIONS

This application claims the benefit of U.S. provisional application Ser. No. 61/250,648 filed Oct. 12, 2009.

The present disclosure is generally directed to antiviral compounds, and more specifically directed to combinations of compounds which can inhibit Hepatitis C virus (HCV), compositions comprising such compounds, and methods for treating Hepatitis C using such combinations.

HCV is a major human pathogen, infecting an estimated 170 million persons worldwide—roughly five times the number infected by human immunodeficiency virus type 1. A substantial fraction of these HCV infected individuals develop serious progressive liver disease, including cirrhosis and hepatocellular carcinoma.

HCV is a positive-stranded RNA virus. Based on a comparison of the deduced amino acid sequence and the extensive similarity in the 5' untranslated region, HCV has been classified as a separate genus in the Flaviviridae family. All members of the Flaviviridae family have enveloped virions that contain a positive stranded RNA genome encoding all known virus-specific proteins via translation of a single, uninterrupted, open reading frame.

Considerable heterogeneity is found within the nucleotide and encoded amino acid sequence throughout the HCV genome due to the high error rate of the encoded RNA dependent RNA polymerase which lacks a proof-reading capability. At least six major genotypes have been characterized, and more than 50 subtypes have been described with distribution worldwide. The clinical significance of the genetic heterogeneity of HCV has demonstrated a propensity for mutations to arise during monotherapy treatment, thus additional treatment options for use are desired. The possible modulator effect of genotypes on pathogenesis and therapy remains elusive. The single strand HCV RNA genome is approximately 9500 nucleotides in length and has a single open reading frame (ORF) encoding a single large polyprotein of about 3000 amino acids. In infected cells, this polyprotein is cleaved at multiple sites by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases. The first one is believed to be a metalloprotease and cleaves at the NS2-NS3 junction; the second one is a serine protease contained within the N-terminal region of NS3 (also referred to herein as NS3 protease) and mediates all the subsequent cleavages downstream of NS3, both in cis, at the NS3-NS4A cleavage site, and in trans, for the remaining NS4A-NS4B, NS4B-NS5A, NS5A-NS5B sites. The NS4A protein appears to serve multiple functions by both acting as a cofactor for the NS3 protease and assisting in the membrane localization of NS3 and other viral replicase components. The formation of a NS3-NS4A complex is necessary for proper protease activity resulting in increased proteolytic efficiency of the cleavage events. The NS3 protein also exhibits nucleoside triphosphatase and RNA helicase activities. NS4B is an integral membrane protein involved in formation of the membranous web where HCV replication complexes are though to assemble. NS5B (also referred to herein as HCV polymerase) is a RNA-dependent RNA polymerase that is involved in the replication of HCV with other HCV proteins, including NS5A, in a replicase complex.

The current standard of care for treatment of most patients with chronic HCV infection is a regimen of pegylated interferon-alpha and ribavirin. However, a high proportion of patients fail to respond to this therapy and treatment is associated with significant side effects. Thus, there is a great need to develop safer and more effective therapies. Although a number of small molecule HCV inhibitors are currently in clinical trials, based on clinical data from several studies it is evident that combinations of inhibitors may be required to effect sustained viral response in HCV infected patients. Resistance emergence in patients during treatment, and posttreatment viral rebound, have been observed upon treatment with protease inhibitors, as well as, nucleoside and non-nucleoside HCV inhibitors. To achieve maximal efficacy and to potentially eradicate the virus, it will be critical to utilize combination therapies, especially those targeting distinct HCV viral targets. In vitro replicon-based combination studies have shown that additive to synergistic effects can be achieved with various combinations of HCV inhibitors.

Commonly owned patent application WO2008/021927 discloses compounds which inhibit the function of the NS5A protein encoded by HCV. U.S. Pat. No. 6,995,174 discloses compounds which inhibit the function of the NS3 protease encoded by HCV. The present disclosure teaches combinations of a specific HCV NS5A inhibitor and an HCV NS3 protease inhibitor that are useful for the treatment of HCV.

In its first aspect the present disclosure provides a composition comprising a therapeutically effective amount of a compound of formula (I)

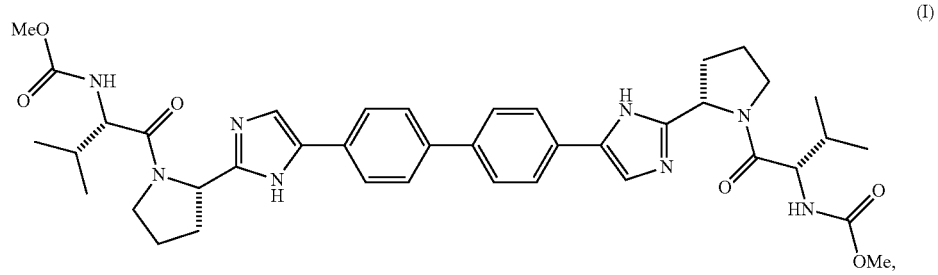 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]

or a pharmaceutically acceptable salt thereof, and a therapeutically effective amount of a compound of formula (II),

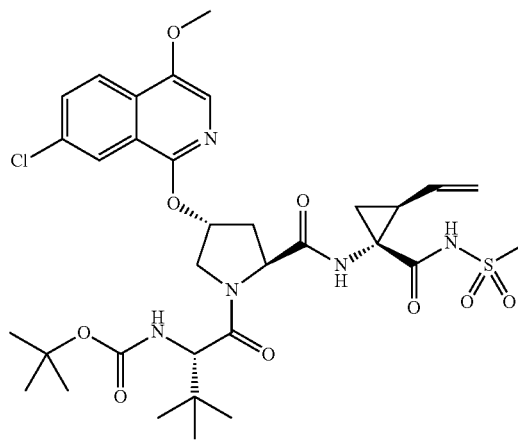

(II)

or a pharmaceutically acceptable salt thereof, and a pharmaceutically acceptable carrier. In a first embodiment of the first aspect the ratio of the compound of formula (I), or a pharmaceutically acceptable salt thereof, to the compound of formula (II), or a pharmaceutically acceptable salt thereof, is between about 1:3 and about 3:1. In a second embodiment of the first aspect the ratio of the compound of formula (I), or a pharmaceutically acceptable salt thereof, to the compound of formula (II), or a pharmaceutically acceptable salt thereof, is between about 1:2.5 and about 2.5:1. In a third embodiment of the first aspect the ratio of the compound of formula (I), or a pharmaceutically acceptable salt thereof, to the compound of formula (II), or a pharmaceutically acceptable salt thereof is about 1:1. In a fourth embodiment of the first aspect the ratio of the compound of formula (I), or a pharmaceutically acceptable salt thereof, to the compound of formula (II), or a pharmaceutically acceptable salt thereof, is about 1:2.5. In a fifth embodiment of the first aspect the ratio of the compound of formula (I), or a pharmaceutically acceptable salt thereof, to the compound of formula (II), or a pharmaceutically acceptable salt thereof, is about 2.5:1.

In a sixth embodiment of the first aspect the present disclosure provides a composition comprising a therapeutically effective amount of a compound of formula (I)

or a pharmaceutically acceptable salt thereof, and a therapeutically effective amount of a compound of formula (II),

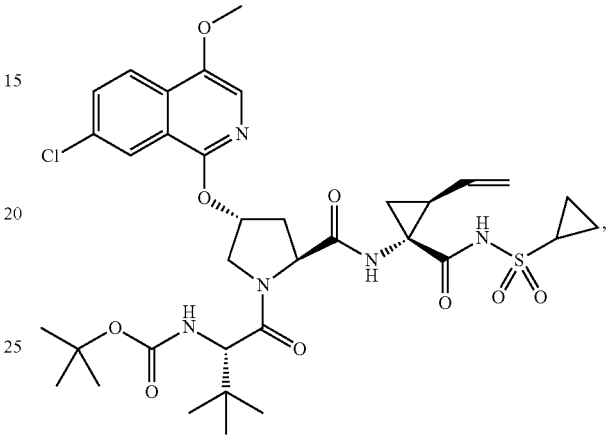

(II)

or a pharmaceutically acceptable salt thereof, one or two additional compounds having anti-HCV activity, and a pharmaceutically acceptable carrier. In a seventh embodiment at least one of the additional compounds is an interferon or a ribavirin. In an eighth embodiment the interferon is selected from interferon alpha 2B, pegylated interferon alpha, interferon lambda, pegylated interferon lambda, consensus interferon, interferon alpha 2A, and lymphoblastoid interferon tau.

In a second aspect the present disclosure provides a method of treating an HCV infection in a patient, comprising administering to the patient a therapeutically effective amount of a composition comprising a therapeutically effective amount of a compound of formula (I)

(I)

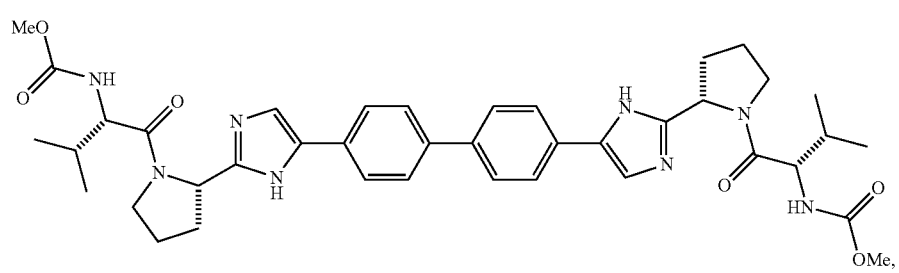

(I)

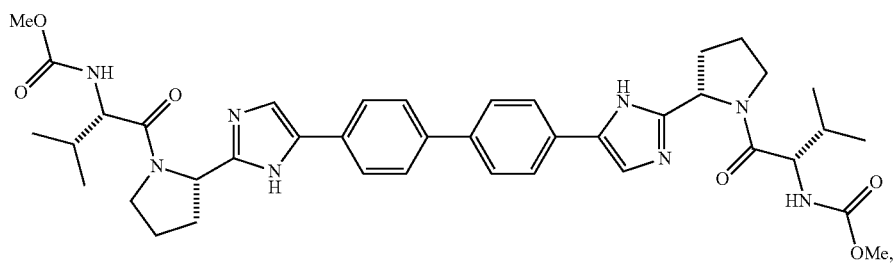

or a pharmaceutically acceptable salt thereof, and a therapeutically effective amount of a compound of formula (II), (II)

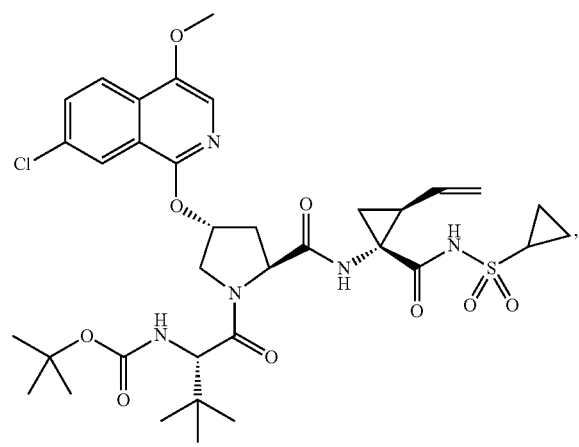

or a pharmaceutically acceptable salt thereof, and a pharmaceutically acceptable carrier. In a first embodiment of the second aspect the ratio of the compound of to formula (I), or a pharmaceutically acceptable salt thereof, to the compound of formula (II), or a pharmaceutically acceptable salt thereof, is between about 1:3 and about 3:1. In a second embodiment of the second aspect the ratio of the compound of formula (I), or a pharmaceutically acceptable salt thereof, to the compound of formula (II), or a pharmaceutically acceptable salt thereof, is between about 1:2.5 and about 2.5:1. In a third embodiment of the second aspect the ratio of the compound of formula (I), or a pharmaceutically acceptable salt thereof, to the compound of formula (II), or a pharmaceutically acceptable salt thereof is about 1:1. In a fourth embodiment of the second aspect the ratio of the compound of formula (I), or a pharmaceutically acceptable salt thereof, to the compound of formula (II), or a pharmaceutically acceptable salt thereof, is about 1:2.5. In a fifth embodiment of the second aspect the ratio of the compound of formula (I), or a pharmaceutically acceptable salt thereof, to the compound of formula (II), or a pharmaceutically acceptable salt thereof, is about 2.5:1.

In a sixth embodiment of the first aspect the present disclosure provides a method of treating an HCV infection in a patient, comprising administering to the patient a therapeutically effective amount of a composition comprising a therapeutically effective amount of a compound of formula (I)

(I)

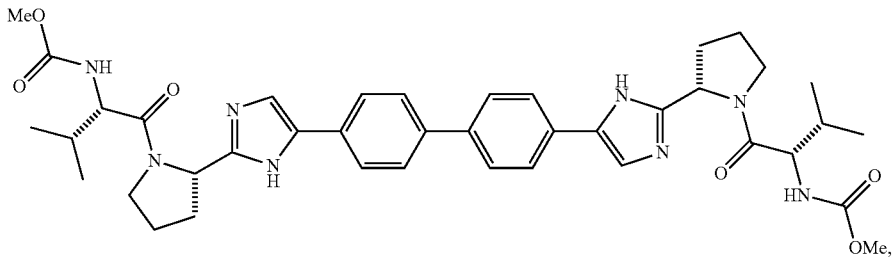

or a pharmaceutically acceptable salt thereof, and a therapeutically effective amount of a compound of formula (II), (II)

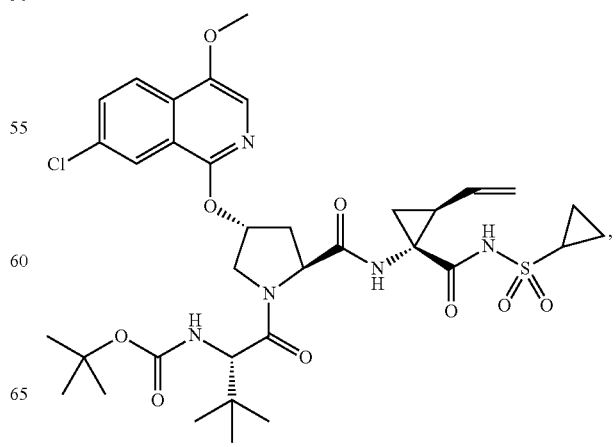

or a pharmaceutically acceptable salt thereof, and a pharmaceutically acceptable carrier, further comprising administering one or two additional compound having anti-HCV activity prior to, after or simultaneously with said composition. In a seventh embodiment at least one of the additional compounds is an interferon or a ribavirin. In an eighth embodiment the interferon is selected from interferon alpha 2B, pegylated interferon alpha, interferon lambda, pegylated interferon lambda, consensus interferon, interferon alpha 2A, and lymphoblastoid interferon tau.

In a third aspect the present disclosure provides a composition comprising a therapeutically effective amount of a compound of formula (I)

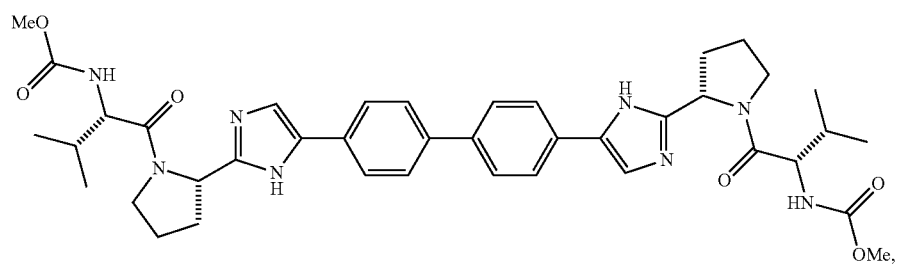

(I)

or a pharmaceutically acceptable salt thereof, and a therapeutically effective amount of a compound of formula (II)

(II)

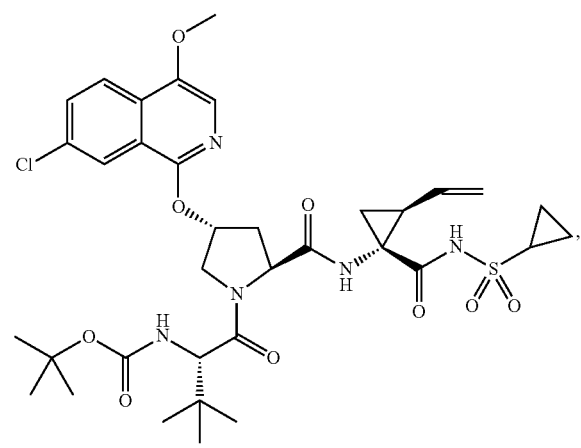

or a pharmaceutically acceptable salt thereof, and a pharmaceutically acceptable carrier, wherein the ratio of the compound of formula (I), or a pharmaceutically acceptable salt thereof, to the compound of formula (II), or a pharmaceutically acceptable salt thereof, is about 1:10.

Other aspects of the present disclosure may include suitable combinations of embodiments disclosed herein.

Yet other aspects and embodiments may be found in the description provided herein.

All patents, patent applications, and literature references cited in the specification are herein incorporated by reference in their entirety. In the case of inconsistencies, the present disclosure, including definitions, will prevail.

As used in the present specification, the following terms have the meanings indicated:

As used herein, the singular forms "a", "an", and "the" include plural reference unless the context clearly dictates otherwise.

Certain compounds of the present disclosure may exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthalenesulfonate, nicotinate, 2-naphthalenesulfonate, oxalate, palmoate, pectinate, persulfate, 3-phenylpropionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting an acidic proton with a suitable base such as the hydroxide, carbonate, or bicarbonate of a metal cation or with ammonia or an organic primary, secondary, or tertiary amine The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine Other representative organic amines useful for the formation of base addition salts include ethylenediamine, ethanolamine, diethanolamine, piperidine, and piperazine.

The disclosure provides pharmaceutical compositions, which include therapeutically effective amounts of compounds of Formulae (I) and (II), or pharmaceutically acceptable salts thereof, and one or more pharmaceutically acceptable carriers, diluents, or excipients. The term "therapeutically effective amount," as used herein, refers to the total amount of each active component that is sufficient to show a meaningful patient benefit, e.g., a sustained reduction in viral load. When applied to an individual active ingredient, administered alone, the term refers to that ingredient alone. When applied to a combination, the term refers to combined amounts of the active ingredients that result in the therapeutic effect, whether administered in combination, serially, or simultaneously. The compounds of Formulae (I) and (II) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the present disclosure there is also provided a process for the preparation of a pharmaceutical formulation including admixing compounds of Formulae (I) and (II), or pharmaceutically acceptable salts thereof, with one or more pharmaceutically acceptable carriers, diluents, or excipients. The term "pharmaceutically acceptable," as used herein, refers to those compounds, materials, compositions, and/or dosage forms which are, within the scope of sound medical judgment, suitable for use in contact with the tissues of patients without excessive toxicity, irritation, allergic response, or other problem or complication commensurate with a reasonable benefit/risk ratio, and are effective for their intended use.

Pharmaceutical formulations may be presented in unit dose forms containing a predetermined amount of active ingredients per unit dose. Typically, the pharmaceutical compositions of this disclosure will be administered from about 1 to about 5 times per day or alternatively, as a continuous infusion. Such administration can be used as a chronic or acute therapy. The amount of active ingredient that may be combined with the carrier materials to produce a single dosage form will vary depending on the condition being treated, the severity of the condition, the time of administration, the route of administration, the rate of excretion of the compound employed, the duration of treatment, and the age, gender, weight, and condition of the patient. Preferred unit dosage formulations are those containing a daily dose or sub-dose, as herein above recited, or an appropriate fraction thereof, of an active ingredient. Generally, treatment is initiated with small dosages substantially less than the optimum dose of the compound. Thereafter, the dosage is increased by small increments until the optimum effect under the circumstances is reached. In general, the compound is most desirably administered at a concentration level that will generally afford antivirally effective results without causing any harmful or deleterious side effects.

As the compositions of this disclosure comprise a combination of two compounds having anti-HCV activity, both compounds can be present in a dose that is less than or equal to the dosage normally administered in a monotherapy regimen. Dosage levels of between about 0.01 and about 250 milligram per kilogram ("mg/kg") body weight per day, preferably between about 0.05 and about 100 mg/kg body weight per day of each of the compounds of the present disclosure are typical in a monotherapy for the prevention and treatment of HCV mediated disease. The compositions of this disclosure may be co-formulated with one or more additional therapeutic or prophylactic agents, for example, in the form of a monolithic and/or bi/multi-layer tablet or may be administered separately from the therapeutic or prophylactic agent(s).

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formulae (I) and (II), and pharmaceutically acceptable salts thereof, can also be administered in the form of liposome delivery systems, such as small unilamellar vesicles, large unilamellar vesicles, and multilamellar vesicles.

Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The term "patient" includes both human and other mammals. The term "treating" refers to: (i) preventing a disease, disorder or condition from occurring in a patient that may be predisposed to the disease, disorder, and/or condition but has not yet been diagnosed as having it; (ii) inhibiting the disease, disorder, or condition, i.e., arresting its development; and (iii) relieving the disease, disorder, or condition, i.e., causing regression of the disease, disorder, and/or condition.

Table 1 below lists some illustrative examples of compounds that can be administered with the compositions of this disclosure. The compositions of the disclosure can be administered with other anti-HCV activity compounds in combination therapy, either jointly or separately, or by combining the compounds into a composition.

TABLE 1

| Brand Name | Physiological Class | Type of Inhibitor or Target | Source Company |
|---|---|---|---|
| NIM811 | | Cyclophilin inhibitors | Novartis |
| Debio-025 | | | Debiopharm |
| SCY-635 | | | Scynexis |

TABLE 1-continued

| Brand Name | Physiological Class | Type of Inhibitor or Target | Source Company |
|---|---|---|---|
| Zadaxin | | Immuno-modulator | Sciclone |
| Suvus | | Methylene blue | Bioenvision |
| Actilon (CPG10101) | | TLR9 agonist | Coley |
| Batabulin (T67) | Anticancer | β-Tubulin inhibitor | Tularik Inc., South San Francisco, CA |
| ISIS 14803 | Antiviral | Antisense | ISIS Pharmaceuticals Inc, Carlsbad, CA/Elan Pharmaceuticals Inc., New York, NY |
| Summetrel | Antiviral | Antiviral | Endo Pharmaceuticals Holdings Inc., Chadds Ford, PA |
| GS-9132 (ACH-806) | Antiviral | HCV inhibitor | Achillion/Gilead |
| Pyrazolopyrimidine compounds and salts From WO2005/047288 26 May 2005 | Antiviral | HCV inhibitors | Arrow Therapeutics Ltd. |
| Levovirin | Antiviral | IMPDH inhibitor | Ribapharm Inc., Costa Mesa, CA |
| Merimepodib (VX-497) | Antiviral | IMPDH inhibitor | Vertex Pharmaceuticals Inc., Cambridge, MA |
| XTL-6865 (XTL-002) | Antiviral | Monoclonal antibody | XTL Biopharmaceuticals Ltd., Rehovot, Israel |
| Telaprevir (VX-950, LY-570310) | Antiviral | NS3 serine protease inhibitor | Vertex Pharmaceuticals Inc., Cambridge, MA/Eli Lilly and Co. Inc., Indianapolis, IN |
| HCV-796 | Antiviral | NS5B replicase inhibitor | Wyeth/Viropharma |
| NM-283 | Antiviral | NS5B replicase inhibitor | Idenix/Novartis |
| GL-59728 | Antiviral | NS5B replicase inhibitor | Gene Labs/Novartis |
| GL-60667 | Antiviral | NS5B replicase inhibitor | Gene Labs/Novartis |
| 2'C MeA | Antiviral | NS5B replicase inhibitor | Gilead |
| PSI 6130 | Antiviral | NS5B replicase inhibitor | Roche |
| R1626 | Antiviral | NS5B replicase inhibitor | Roche |
| 2'C Methyl adenosine | Antiviral | NS5B replicase inhibitor | Merck |
| JTK-003 | Antiviral | RdRp inhibitor | Japan Tobacco Inc., Tokyo, Japan |
| Levovirin | Antiviral | Ribavirin | ICN Pharmaceuticals, Costa Mesa, CA |
| Ribavirin | Antiviral | Ribavirin | Schering-Plough Corporation, Kenilworth, NJ |
| Viramidine | Antiviral | Ribavirin prodrug | Ribapharm Inc., Costa Mesa, CA |
| Heptazyme | Antiviral | Ribozyme | Ribozyme Pharmaceuticals Inc., Boulder, CO |
| BILN-2061 | Antiviral | Serine protease inhibitor | Boehringer Ingelheim Pharma KG, Ingelheim, Germany |
| SCH-900518-narleprevir | Antiviral | Serine protease inhibitor | Schering Plough |
| Zadazim | Immune modulator | Immune modulator | SciClone Pharmaceuticals Inc., San Mateo, CA |
| Ceplene | Immunomodulator | Immune modulator | Maxim Pharmaceuticals Inc., San Diego, CA |

TABLE 1-continued

| Brand Name | Physiological Class | Type of Inhibitor or Target | Source Company |
|---|---|---|---|
| CellCept | Immunosuppressant | HCV IgG immuno-suppressant | F. Hoffmann-La Roche LTD, Basel, Switzerland |
| Civacir | Immunosuppressant | HCV IgG immuno-suppressant | Nabi Biopharmaceuticals Inc., Boca Raton, FL |
| Albuferon-α | Interferon | Albumin IFN-α2b | Human Genome Sciences Inc., Rockville, MD |
| Infergen A | Interferon | IFN alfacon-1 | InterMune Pharmaceuticals Inc., Brisbane, CA |
| Omega IFN | Interferon | IFN-ω | Intarcia Therapeutics |
| IFN-β and EMZ701 | Interferon | IFN-β and EMZ701 | Transition Therapeutics Inc., Ontario, Canada |
| Rebif | Interferon | IFN-β1a | Serono, Geneva, Switzerland |
| Roferon A | Interferon | IFN-α2a | F. Hoffmann-La Roche LTD, Basel, Switzerland |
| Intron A | Interferon | IFN-α2b | Schering-Plough Corporation, Kenilworth, NJ |
| Intron A and Zadaxin | Interferon | IFN-α2b/α1-thymosin | RegeneRx Biopharma. Inc., Bethesda, MD/ SciClone Pharmaceuticals Inc, San Mateo, CA |
| Rebetron | Interferon | IFN-α2b/ribavirin | Schering-Plough Corporation, Kenilworth, NJ |
| Actimmune | Interferon | INF-γ | InterMune Inc., Brisbane, CA |
| Interferon-β | Interferon | Interferon β-1a | Serono |
| Multiferon | Interferon | Long lasting IFN | Viragen/Valentis |
| Wellferon | Interferon | Lymphoblastoid IFN-αn1 | GlaxoSmithKline plc, Uxbridge, UK |
| Omniferon | Interferon | natural IFN-α | Viragen Inc., Plantation, FL |
| Pegasys | Interferon | PEGylated IFN-α2a | F. Hoffmann-La Roche LTD, Basel, Switzerland |
| Pegasys and Ceplene | Interferon | PEGylated IFN-α2a/ immune modulator | Maxim Pharmaceuticals Inc, San Diego, CA |
| Pegasys and Ribavirin | Interferon | PEGylated IFN-α2a/ ribavirin | F. Hoffmann-La Roche LTD, Basel, Switzerland |
| PEG-Intron | Interferon | PEGylated IFN-α2b | Schering-Plough Corporation, Kenilworth, NJ |
| PEG-Intron/Ribavirin | Interferon | PEGylated IFN-α2b/ ribavirin | Schering-Plough Corporation, Kenilworth, NJ |
| IP-501 | Liver protection | Antifibrotic | Indevus Pharmaceuticals Inc., Lexington, MA |
| IDN-6556 | Liver protection | Caspase inhibitor | Idun Pharmaceuticals Inc., San Diego, CA |
| ITMN-191 (R-7227) | Antiviral | Serine protease inhibitor | InterMune Pharmaceuticals Inc., Brisbane, CA |
| GL-59728 | Antiviral | NS5B replicase inhibitor | Genelabs |
| ANA-971 | Antiviral | TLR-7 agonist | Anadys |
| Boceprevir | Antiviral | Serine protease inhibitor | Schering Plough |
| TMC-435 | Antiviral | Serine protease inhibitor | Tibotec BVBA, Mechelen, Belgium |

TABLE 1-continued

| Brand Name | Physiological Class | Type of Inhibitor or Target | Source Company |
|---|---|---|---|
| BI-201335 | Antiviral | Serine protease inhibitor | Boehringer Ingelheim Pharma KG, Ingelheim, Germany |
| MK-7009 | Antiviral | Serine protease inhibitor | Merck |
| MK-5172 | Antiviral | Serine protease inhibitor | Merck |
| IDX-316 | Antiviral | Serine protease inhibitor | Idenix |
| ACH-1625 | Antiviral | Serine protease inhibitor | Achillion |
| ACH-2684 | Antiviral | Serine protease inhibitor | Achillion |
| AVL-181 | Antiviral | Serine protease inhibitor | Avila |
| ABT-450 | Antiviral | Serine protease inhibitor | Abbott/Enanta |
| GS-9256 | Antiviral | Serine protease inhibitor | Gilead |
| ITMN-8187 | Antiviral | Serine protease inhibitor | Intermune |
| PF-00868554 (filibuvir) | Antiviral | Replicase inhibitor | Pfizer |
| ANA598 | Antiviral | Non-Nucleoside NS5B polymerase inhibitor | Anadys Pharmaceuticals, Inc., San Diego, CA, USA |
| IDX375 | Antiviral | Non-Nucleoside replicase inhibitor | Idenix Pharmaceuticals, Cambridge, MA, USA |
| BILB 1941 | Antiviral | NS5B polymerase inhibitor | Boehringer Ingelheim Canada Ltd R&D, Laval, QC, Canada |
| PSI-7851 | Antiviral | Nucleoside polymerase inhibitor | Pharmasset, Princeton, NJ, USA |
| PSI-352938 | Antiviral | Nucleoside polymerase inhibitor | Pharmasset, Princeton, NJ, USA |
| PSI-7977 | Antiviral | Nucleoside polymerase inhibitor | Pharmasset, Princeton, NJ, USA |
| TMC-647055 | Antiviral | Nucleoside polymerase inhibitor | Tibotec/Medivir |
| INX-189 | Antiviral | Nucleoside polymerase inhibitor | Inhibitex |
| VCH-759 | Antiviral | NS5B polymerase inhibitor | ViroChem Pharma |
| VCH-916 | Antiviral | NS5B polymerase inhibitor | ViroChem Pharma |
| GS-9190 | Antiviral | NS5B polymerase inhibitor | Gilead |
| PPI-461 | Antiviral | NS5A inhibitor | Presidio |
| PPI-1310 | Antiviral | NS5A inhibitor | Presidio |
| GS-5885 | Antiviral | NS5A inhibitor | Gilead |
| EDP-239 | Antiviral | NS5A inhibitor | Enanta |
| ACH-2928 | Antiviral | NS5A inhibitor | Achillion |
| ITX-5061 | Host cell entry receptor inhibitor | HCV entry inhibitor SR-B1 antagonist | itherX |
| Peg-interferon lamda | Antiviral | Interferon | ZymoGenetics/ Bristol-Myers Squibb |

The compositions of the present disclosure may also be used as laboratory reagents. Compounds may be instrumental in providing research tools for designing of viral replication assays, validation of animal assay systems and structural biology studies to further enhance knowledge of the HCV disease mechanisms. Further, the compounds of the present disclosure are useful in establishing or determining the binding site of other antiviral compounds, for example, by competitive inhibition.

The compounds of this disclosure may also be used to treat or prevent viral contamination of materials and therefore reduce the risk of viral infection of laboratory or medical personnel or patients who come in contact with such materials, e.g., blood, tissue, surgical instruments and garments, laboratory instruments and garments, and blood collection or transfusion apparatuses and materials.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

Starting materials can be obtained from commercial sources or prepared by well-established literature methods known to those of ordinary skill in the art.

EXAMPLES

Compounds

The HCV NS5A inhibitor (compound of formula (I)) can be prepared following the procedure described in commonly owned patent applications WO2008/021927 or WO2009/020825. The HCV NS3 inhibitor (compound of formula (II)) can be prepared following the procedure described in commonly owned U.S. Pat. No. 6,995,174 and commonly owned U.S. patent application Ser. No. 12/547,158. Recombinant IL-29 (rIL-29 or rIFNλ1) is expressed in *E. coli* as a modified N-terminal methionylated form of human IL-29. Recombinant IL-28A (rIFNλ2) and rIL28B (rIFNλ3) are also expressed in *E. coli*. Pegylated rIFNλ1 (pegIFNλ) is a covalent conjugate of rIFNλ1 (molecular weight of 19.6 kDa) and a 20 kDa linear polyethylene glycol (peg) chain. Both rIFNλ1 and pegIFNλ, synthesized by Zymogenetics, have been extensively characterized by a number of methods, including amino acid analysis, N-terminal sequencing, size exclusion\ chromatography-multi-angle light scattering (SEC-MALS), peptide map analysis, and whole mass analysis. The combined analyses for rIFNλ1 confirm that the purified protein is predominantly of 1 form, with 2 disulfide bonds in the expected conformation. In addition, the analyses confirm that the sequence is as expected based on the cDNA sequence and expression in *E. coli*, in that the protein has an additional N-terminal methionine and no glycosylation. The combined analysis for pegIFNλ confirms that the protein part of the molecule is still in the expected form and with the expected conformation. In addition, the analyses demonstrated that the molecule is predominantly pegylated on the N-terminus, as expected. The analysis by SEC-MALS and whole mass spectrometry confirm that the molecular weight is approximately 39.6 kDa, as expected from conjugation of rIFNλ1 with 20 kDa peg.

Cell Lines

The Huh-7 cell-line used for these studies was obtained from Dr. Ralf Bartenschlager (University of Heidelberg, Heidelberg, Germany) and was propagated in DMEM containing 10% FBS, 10 U/ml penicillin and 10 μg/ml streptomycin. The HCV replicons used in these studies were generated at Bristol-Myers Squibb using the procedure described in WO2004014852. The coding sequence of the published genotype 1b HCV replicon (Lohmann, V., F. Korner, J.-O. Koch, U. Herian, L. Theilmann, and R. Bartenschlager 1999, *Science* 285:110-113) was synthesized by Operon Technologies, Inc. (Alameda, Calif.) using the sequence set forth in EMBL Accession No. AJ242652, nucleotides 1801 to 7758. The functional replicon was then assembled in plasmid pGem9zf(+) (Promega, Madison, Wis.) using standard molecular biology techniques. To create a replicon encoding a luciferase reporter, the gene encoding humanized *Renilla* Luciferase protein was introduced upstream of the neomycin phosphotransferase gene. The resulting replicon consists of (i) the HCV 5' UTR fused to the first 12 amino acids of the capsid protein, (ii) the renilla luciferase gene, (iii) the neomycin phosphotransferase gene (neo), (iv) the IRES from encephalomyocarditis virus (EMCV), and (v) HCV NS3 to NS5B genes and the HCV 3' UTR.

The 1a replicon was generated using the clone described above by replacing 1b HCV sequence with genotype 1a sequence from pCV-H77c (Yanagi, M., R. Purcell, S. Emerson, J. Bukh 1997, *PNAS*, 94:8738-8743; Jens Bukh, National Institute of Health, Bethesda, Md. 20892) using standard molecular cloning techniques. In order to obtain a more efficient 1a replicon, adaptive mutations P1496L (NS3) and S2204I (NS5A) were introduced using a Quick Change XL Site-Directed Mutagenesis Kit as described by the manufacturer (Stratagene Corporation, La Jolla, Calif.).

HCV replicon cell lines were isolated from colonies as described by Lohman, et. al (Lohmann, V., F. Korner, J.-O. Koch, U. Herian, L. Theilmann, and R. Bartenschlager 1999, *Science* 285:110-113) and used for all experiments. Briefly, replicon clones were linearized with ScaI and RNA transcripts synthesized in vitro using the T7 MegaScript transcription kit (Ambion, Austin, Tex.) according to manufacturer's directions. Ten to 20 μg of in vitro transcribed replicon RNA was introduced into $4-5\times10^6$ Huh-7 cells by transfection with DMRIE-C reagent (Invitrogen Corporation, Carlsbad, Calif.) following manufacturer's protocols. After 24 h, selective media containing 0.5 mg/mL Geneticin (G418, Gibco-BRL, Rockville, Md.) was added and media was changed every 3 to 5 days. After approximately 4 weeks, cells were expanded for further analysis. Cells were maintained at 37° C. in DMEM (Gibco-BRL, Rockville, Md.) with 10% heat inactivated calf serum (Sigma), penicillin/streptomycin, and 0.5 mg/ml G418.

Cell Culture Cytotoxicity and Luciferase Assays

To determine compound efficacy, HCV replicon cells were plated at a density of $10^4$ per well in 96-well plates in DMEM media containing 10% FBS. Following incubation overnight, compounds serially diluted in DMSO, or DMSO alone, were added to individual wells to a final DMSO concentration of 0.5%. Cell plates were then incubated at 37° C. for 3 days prior to assaying for cytotoxicity and HCV inhibition. Cell viability was measured using an Alamar blue assay and $CC_{50}$ values were calculated using the median effect equation.

Plates were then washed two times with PBS and renilla luciferase activity assayed using a Dual-Glo Luciferase Assay System (Promega Corporation, Madison, Wis.) according to the manufacturer's directions. Plates were read on a TopCount NXT Microplate Scintillation and Luminescence Counter (Packard Instrument Company). The 50% effective concentration ($EC_{50}$) was calculated by using Excel Fit (Version 2.0, Build 30). Known x (compound concentration) and y (% relative to DMSO-only control wells) values were used to calculate the $EC_{50}$ with Excel Fit equation 205, represented as $y=A+((B-A)/(1+((C/x)^D)))$, where A and B equal the bottom and top plateaus of the curve, respectively, C equals the x value at the middle of the curve, and D equals the slope factor.

Combination Studies

For inhibitor combination studies, IFN-α and inhibitors of HCV NS5A and the NS3 protease were each tested at eleven concentrations. Stock solutions, 200 times the desired final assay concentration, were prepared by 3-fold dilution in DMSO prior to addition to cells/media. The compounds were tested as monotherapies and in combinations with the compound of formula (I) at various concentration ratios. Cells were exposed to compounds for 3 days and the amount of HCV inhibition was then determined using the luciferase assay as described above. The potential cytotoxicities of these combined agents were also analyzed in parallel by Alamar blue staining. The degree of antagonism, additivity, or synergy was determined over a range of drug concentrations, and combination response curves were fit to assess the antiviral effects of the drug treatment combinations. The combined effect of the drugs in combination was analyzed using the method of Chou Chou T. Theoretical Basis, Experimental Design, and Computerized Simulation of Synergism and Antagonism in Drug Combination Studies. Pharmacological Reviews. 2006; 58(3):621-81.

All estimates were computed using biostatistical software SAS Proc NLIN, and a four-parameter logistic. All combination indices were tested for departure from additivity using isobologram methods. Asymptotic confidence intervals were also calculated for each of the combination indices. These intervals are used to test for departure from additivity by comparing the bounds to one—a lower bound of the interval greater than 1 indicates antagonism, an upper bound of less than 1 indicates synergism, and a value of 1 contained in the interval indicates additivity.

Results

Resistance to antiviral therapy has become a major issue in the management of patients with chronic viral infections. To achieve sustained viral responses, it will be critical to utilize combination therapies, especially those targeting distinct HCV viral targets. In this report, we use the HCV replicon to assess the degree of antagonism, additivity or synergy when combining the HCV NS5A inhibitor of formula (I) with the NS3 protease inhibitor of formula (II), as well as comparing the effect when combining IFN-α, pegIFNλ, or rIFNλ1 with both compounds.

For the experiments shown in Tables 2-6, the NS5A inhibitor of formula (I) and the NS3 Protease inhibitor of formula (II) were tested in combination either alone or with various interferons using the HCV replicon system, and the estimated $EC_{50}$ values for each as well as the combination indices (CI), are reported. The potential cytotoxicities of these combined agents were also analyzed in parallel and none reached $CC_{50}$ values.

Combination of the NS5A inhibitor of formula (I) with the NS3 protease inhibitor of formula (II) was evaluated in both genotype 1a and 1b replicon cells. As shown in Table 2, the overall results from two experiments on genotype 1a indicate additivity with synergistic effects observed in one experiment at the 75% and 95% effective doses at the 2.5:1 ratio of NS5A inhibitor to NS3 protease inhibitor.

TABLE 2

Combination of HCV NS5A Inhibitor of Formula (I) with NS3 Protease Inhibitor of Formula (II) on Genotype 1a

| Expt | NS5A Inhibitor $EC_{50}$, nM | NS3 Protease Inhibitor $EC_{50}$, nM | Ratio, NS5A Inhibitor to NS3 Inhibitor | Combination Indices (confidence interval) | | | Overall Result |
|---|---|---|---|---|---|---|---|
| | | | | 50% effective | 75% effective | 90% effective | |
| 1 | 0.045 | 8.5 | 1:1 | 0.98 (0.89, 1.07) | 0.91 (0.79, 1.03) | 0.86 (0.69, 1.03) | Additivity |
| | | | 1:2.5 | 0.96 (0.86, 1.05) | 0.95 (0.82, 1.09) | 0.97 (0.75, 1.18) | Additivity |
| | | | 2.5:1 | 0.96 (0.88, 1.03) | 0.84 (0.75, 0.94) | 0.76 (0.60, 0.91) | Additivity/ Synergy |
| 2 | 0.037 | 7.8 | 1:1 | 0.97 (0.89, 1.05) | 0.96 (0.85, 1.07) | 0.97 (0.80, 1.14) | Additivity |
| | | | 1:2.5 | 0.99 (0.91, 1.07) | 0.98 (0.87, 1.09) | 0.98 (0.81, 1.15) | Additivity |
| | | | 2.5:1 | 0.93 (0.85, 1.00) | 0.98 (0.88, 1.09) | 1.05 (0.87, 1.23) | Additivity |

The effects of the NS5A compound of formula (I) in combination with the NS3 protease inhibitor of formula (II) on genotype 1b are summarized in Table 3. Taken as a whole, the results of all three experiments indicate mixed additivity/synergy.

TABLE 3

Combination of NS5A Inibitor of Formula (I) with an NS3 Protease Inhibitor of Formula (II) on Genotype 1b

| Expt | NS5A Inhibitor $EC_{50}$, nM | NS3 Protease Inhibitor $EC_{50}$, nM | Ratio, NS3 Inhibitor to NS3 Inhibitor | Combination Indices (confidence interval) | | | Overall Result |
|---|---|---|---|---|---|---|---|
| | | | | 50% effective | 75% effective | 90% effective | |
| 1 | 0.005 | 0.5 | 1:1 | 0.65 (0.57, 0.73) | 0.72 (0.60, 0.84) | 0.82 (0.60, 1.04) | Synergy/ Additivity |

TABLE 3-continued

Combination of NS5A Inibitor of Formula (I) with an NS3 Protease Inhibitor of Formula (II) on Genotype 1b

| Expt | NS5A Inhibitor $EC_{50}$, nM | NS3 Protease Inhibitor $EC_{50}$, nM | Ratio, NS3 Inhibitor to NS3 Inhibitor | Combination Indices (confidence interval) 50% effective | 75% effective | 90% effective | Overall Result |
|---|---|---|---|---|---|---|---|
| | | | 2.5:1 | 0.77 (0.69, 0.86) | 0.77 (0.65, 0.89) | 0.80 (0.60, 0.99) | Synergy |
| | | | 1:2.5 | 0.57 (0.51, 0.63) | 0.61 (0.52, 0.70) | 0.68 (0.52, 0.84) | Synergy |
| 2 | 0.003 | 0.5 | 1:1 | 0.90 (0.79, 1.01) | 0.97 (0.80, 1.13) | 1.07 (0.79, 1.36) | Additivity |
| | | | 2.5:1 | 0.76 (0.67, 0.85) | 0.82 (0.69, 0.95) | 0.91 (0.68, 1.14) | Synergy/ Additivity |
| | | | 1:2.5 | 0.68 (0.61, 0.76) | 0.78 (0.66, 0.90) | 0.92 (0.70, 1.14) | Synergy/ Additivity |
| 3 | 0.003 | 0.6 | 1:1 | 0.79 (0.72, 0.86) | 0.74 (0.65, 0.82) | 0.69 (0.56, 0.81) | Synergy |
| | | | 2.5:1 | 1.03 (0.93, 1.12) | 0.96 (0.84, 1.07) | 0.89 (0.72, 1.06) | Additivity |
| | | | 1:2.5 | 0.91 (0.83, 0.98) | 0.88 (0.78, 0.97) | 0.85 (0.70, 0.99) | Synergy |

The NS5A inhibitor of formula (I) was also tested in 3-drug combination experiments with IFN-α and the NS3 inhibitor of formula (II) using genotype 1b replicon cells. The results from four experiments show additivity/synergy at 50% and synergy at 75 and 90% effective levels (Table 4).

TABLE 4

Triple Combination Using NS5A Inhibitor of Formula (I) with IFN-α and NS3 Inhibitor of Formula (II)

| Expt | NS5A Inhibitor $EC_{50}$, nM | NS3 Protease Inhibitor $EC_{50}$, nM | IFN-α $EC_{50}$, units per mL | Combination Indices (confidence interval) 50% Effective | 75% Effective | 90% Effective | Overall Result |
|---|---|---|---|---|---|---|---|
| 1 | 0.005 | 1.5 | 6.4 | 0.99 (0.89, 1.08) | 0.87 (0.76, 0.98) | 0.79 (0.64, 0.95) | Additivity/ Synergy |
| 2 | 0.005 | 1.3 | 6.9 | 0.93 (0.85, 1.02) | 0.81 (0.71, 0.91) | 0.72 (0.58, 0.85) | Additivity/ Synergy |
| 3 | 0.006 | 2.2 | 5.9 | 0.88 (0.77, 0.99) | 0.81 (0.69, 0.94) | 0.79 (0.61, 0.97) | Synergy |
| 4 | 0.005 | 1.9 | 2.3 | 0.98 (0.86, 1.10) | 0.83 (0.68, 0.97) | 0.75 (0.55, 0.96) | Additivity/ Synergy |

Triple combinations of pegIFNλ with the NS3 Protease inhibitor of formula (II) and the NS5A inhibitor of formula (I) were tested for additivity. The data from these expts are summarized in Table 5. Additivity was observed in all three expts at the 50% effective level. At the 75 and 90% effective levels, additivity was observed in expts 1 and 3, and synergy in expt 2. Overall, these results indicate mixed additivity and synergy for the combination of pegIFNλ with NS3 protease and NS5A inhibitors. These results are in agreement with results using rIFNλ1 in combination with the NS3 Protease inhibitor of formula (II) and the NS5A inhibitor of formula (I) (Table 6).

TABLE 5

Triple Combination Studies using PegIFNλ, with NS5A Inhibitor of Formula (I) and NS3 Protease Inhibitor of Formula (II)

| Expt | pegIFNλ $EC_{50}$, ng/ml | NS3 Protease Inhibitor $EC_{50}$, nM | NS5A Inhibitor $EC_{50}$, nM | Combination Index (Confidence Interval)[a] 50% Effective | 75% Effective | 90% Effective | Overall Result |
|---|---|---|---|---|---|---|---|
| 1 | 1.8 | 1.1 | 0.004 | 1.04 (0.95, 1.14) | 1.03 (0.91, 1.15) | 1.06 (0.86, 1.25) | Additivity |

TABLE 5-continued

Triple Combination Studies using PegIFNλ, with NS5A Inhibitor of Formula (I) and NS3 Protease Inhibitor of Formula (II)

| | | NS3 | | Combination Index (Confidence Interval)[a] | | | |
|---|---|---|---|---|---|---|---|
| Expt | pegIFNλ EC$_{50}$, ng/ml | Protease Inhibitor EC$_{50}$, nM | NS5A Inhibitor EC$_{50}$, nM | 50% Effective | 75% Effective | 90% Effective | Overall Result |
| 2 | 0.778 | 0.630 | 0.003 | 1.05 (0.95, 1.15) | 0.86 (0.75, 0.98) | 0.77 (0.61, 0.94) | Additivity at 50% Synergy at 75% and 90% |
| 3 | 0.867 | 0.947 | 0.003 | 1.02 (0.94, 1.10) | 0.95 (0.85, 1.06) | 1.00 (0.82, 1.17) | Additivity |

[a]Compounds tested at a ratio of 250/1/1000

TABLE 6

Triple Combination Studies using rIFNλ1 with NS5A Inhibitor of Formula (I) and NS3 Inhibitor of Formula (II)

| | | NS3 | | Combination Index (Confidence Interval)[a] | | | |
|---|---|---|---|---|---|---|---|
| Expt | rIFNλ1 EC$_{50}$, ng/ml | Protease Inhibitor EC$_{50}$, nM | NS5A Inhibitor EC$_{50}$, nM | 50% Effective Level | 75% Effective Level | 90% Effective Level | Overall Result |
| 1 | 0.52 | 1.4 | 0.008 | 0.98 (0.90, 1.06) | 0.96 (0.85, 1.06) | 0.96 (0.79, 1.13) | Additivity |
| 2 | 0.27 | 1.2 | 0.009 | 0.85 (0.76, 0.94) | 0.88 (0.75, 1.02) | 0.97 (0.74, 1.20) | Synergy at 50%, additivity at 75% and 90% effective levels |
| 3 | 0.53 | 2.3 | 0.005 | 0.79 (0.72, 0.86) | 0.80 (0.70, 0.90) | 0.90 (0.72, 1.07) | Synergy at 50% and 75%, additivity at 90% effective levels |

[a]Compounds tested at a ratio of 250/1/1000

These results demonstrate that combination treatment of replicon cells with the NS5A inhibitor of formula (I) and the HCV NS3 protease inhibitor of formula (II), with or without Intron A, rIFNλ1, or pegIFNλ yield additive to synergistic antiviral effects. Importantly, no antagonistic effects or enhanced cytotoxicity were observed with any of these combinations. Therefore, these combinations are excellent candidates for combination regimens in HCV infected patients.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A composition comprising a therapeutically effective amount of a compound of formula (I)

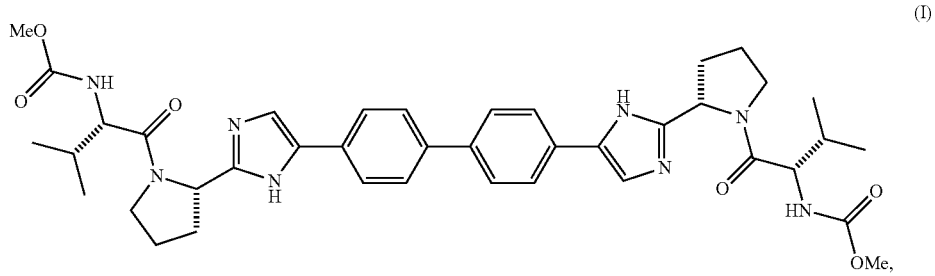 [SMILES: COC(=O)N[C@H](C(=O)N1CCC[C@H]1c1ncc(-c2ccc(-c3ccc(-c4cnc([C@@H]5CCCN5C(=O)[C@@H](NC(=O)OC)C(C)C)[nH]4)cc3)cc2)[nH]1)C(C)C]

or a pharmaceutically acceptable salt thereof, and a therapeutically effective amount of a compound of formula (II),

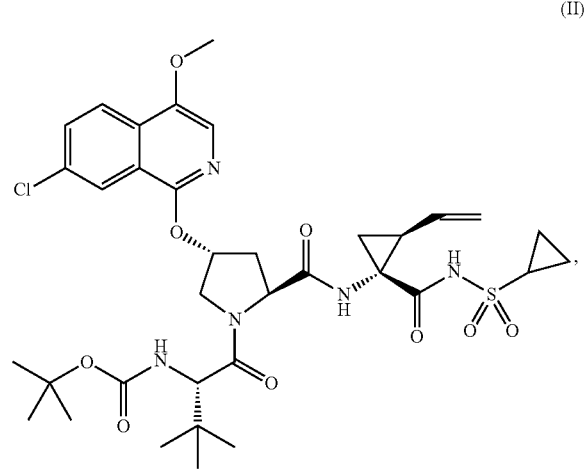 [SMILES: C=C[C@@H]1C[C@]1(NC(=O)[C@@H]1C[C@@H](Oc2ncc(OC)c3ccc(Cl)cc23)CN1C(=O)[C@@H](NC(=O)OC(C)(C)C)C(C)(C)C)C(=O)NS(=O)(=O)C1CC1]

or a pharmaceutically acceptable salt thereof, and a pharmaceutically acceptable carrier, wherein the ratio of the compound of formula (I), or a pharmaceutically acceptable salt thereof, to the compound of formula (II), or a pharmaceutically acceptable salt thereof, is between about 1:3 and about 3:1.

2. The composition of claim 1 wherein the ratio of the compound of formula (I), or a pharmaceutically acceptable salt thereof, to the compound of formula (II), or a pharmaceutically acceptable salt thereof, is between about 1:2.5 and about 2.5:1.

3. The composition of claim 2 wherein the ratio of the compound of formula (I), or a pharmaceutically acceptable salt thereof, to the compound of formula (II), or a pharmaceutically acceptable salt thereof is about 1:1.

4. The composition of claim 2 wherein the ratio of the compound of formula (I), or a pharmaceutically acceptable salt thereof, to the compound of formula (II), or a pharmaceutically acceptable salt thereof, is about 1:2.5.

5. The composition of claim 2 wherein the ratio of the compound of formula (I), or a pharmaceutically acceptable salt thereof, to the compound of formula (II), or a pharmaceutically acceptable salt thereof, is about 2.5:1.

* * * * *

UNITED STATES PATENT AND TRADEMARK OFFICE
CERTIFICATE OF CORRECTION

PATENT NO. : 8,415,374 B2  
APPLICATION NO. : 12/899840  
DATED : April 9, 2013  
INVENTOR(S) : Julie A. Lemm et al.

Page 1 of 1

It is certified that error appears in the above-identified patent and that said Letters Patent is hereby corrected as shown below:

On the Title Page:

Item (56), References Cited, under OTHER PUBLICATIONS:

Column 2, <u>first</u> Lok, A.S. et al. reference, change "PegIFN" to -- PegIFN --.

Column 2, <u>second</u> Lok, A.S. et al. reference, change "PegIFN" to -- PegIFN --.

Signed and Sealed this
Thirteenth Day of May, 2014

Michelle K. Lee
*Deputy Director of the United States Patent and Trademark Office*